(12) United States Patent
Kim et al.

(10) Patent No.: US 9,271,834 B2
(45) Date of Patent: Mar. 1, 2016

(54) SHEATH AND CERCLAGE THREAD FOR MITRAL CERCLAGE ANNULOPLASTY

(71) Applicant: Suntech Co., Seoul (KR)

(72) Inventors: Hyung-Il Kim, Seoul (KR); Il Gyun Shin, Gyeonggi-do (KR)

(73) Assignee: SUNTECH Co., Ltd, Seoul (KR)

( * ) Notice: Subject to any disclaimer, the term of this patent is extended or adjusted under 35 U.S.C. 154(b) by 254 days.

(21) Appl. No.: 14/019,133

(22) Filed: Sep. 5, 2013

(65) Prior Publication Data
US 2014/0067051 A1 Mar. 6, 2014

(30) Foreign Application Priority Data
Sep. 5, 2012 (KR) .......................... 10-2012-0098247

(51) Int. Cl.
*A61F 2/24* (2006.01)

(52) U.S. Cl.
CPC ............. *A61F 2/2466* (2013.01); *A61F 2/2451* (2013.01)

(58) Field of Classification Search
CPC ........... A61B 17/0467; A61B 17/0487; A61B 17/0482; A61B 17/0469; A61B 17/0483; A61B 2017/0496; A61B 2017/0495; A61F 2/2451; A61F 2/2466; A61F 2/2445; A61M 25/0026; A61M 25/09; A61M 25/0102; A61M 2025/0037; A61M 2025/0079; A61M 2025/0293; A61M 2025/0004
USPC ........... 623/2.36–2.38, 2.11, 1.11, 900, 1.26, 623/2.1; 604/500, 508, 510, 507, 164.13, 604/264; 606/148, 139, 144, 228, 108, 74, 606/191; 607/122; 600/585
See application file for complete search history.

(56) References Cited

U.S. PATENT DOCUMENTS

| | | | | |
|---|---|---|---|---|
| 5,336,231 A * | 8/1994 | Adair | ........................... | 606/148 |
| 5,527,322 A * | 6/1996 | Klein et al. | .................... | 606/144 |
| 5,830,229 A * | 11/1998 | Konya et al. | .................. | 606/198 |
| 6,537,314 B2 * | 3/2003 | Langberg et al. | ............ | 623/2.36 |
| 7,347,870 B1 | 3/2008 | Andrieu et al. | | |
| 2003/0233140 A1 * | 12/2003 | Hartley et al. | ............... | 623/1.11 |
| 2004/0181238 A1 * | 9/2004 | Zarbatany et al. | ............ | 606/108 |
| 2005/0283193 A1 * | 12/2005 | Tullberg et al. | ............... | 606/232 |
| 2006/0030885 A1 * | 2/2006 | Hyde | ............................ | 606/232 |
| 2010/0049314 A1 * | 2/2010 | Kim et al. | .................... | 623/2.37 |

FOREIGN PATENT DOCUMENTS

| | | |
|---|---|---|
| JP | 2003-534045 | 2/2003 |
| KR | 1116867 | 3/2011 |
| WO | 2008/060553 | 5/2008 |

OTHER PUBLICATIONS

Kim et al., "Mitral cerclage annuloplasty, a novel transcatheter treatment for second mitral valve regurgitation: Initial results in swine," J. American College Cardiology, 2009, 54(7):638-651.

* cited by examiner

*Primary Examiner* — Jocelin Tanner
(74) *Attorney, Agent, or Firm* — MH2 Technology Law Group, LLP

(57) ABSTRACT

A sheath and cerclage thread for mitral cerclage annuloplasty, where the cerclage thread is inserted into a lumen created independently from the lumen through which the guide wire is passed.

6 Claims, 2 Drawing Sheets

SHEATH AND CERCLAGE THREAD FOR MITRAL CERCLAGE ANNULOPLASTY

CROSS-REFERENCE TO RELATED APPLICATIONS

This application claims priority to and the benefit of Korean Patent Application No. 10-2012-0098247 filed in the Korean Intellectual Property Office on Sep. 5, 2012, the entire contents of which are incorporated herein by reference.

TECHNICAL FIELD

The present invention relates to a sheath and cerclage thread for mitral cerclage annuloplasty. It is characterized by the insertion of the cerclage thread into a lumen created independently from the lumen through which the guide wire is passed. When the sheath of the present invention is used, the surgical time is shortened as the procedure of inserting the thread into the sheath can be omitted, and it has the advantage of using a cerclage thread with reduced rigidity. An advantage of a less rigid cerclage thread is that it is less likely to damage the adjacent cardiac tissue.

BACKGROUND

The heart is an organ that pumps blood. The valves that make the blood flow in a fixed direction without backflow are essential for heart function. There are 4 chambers (2 atria and 2 ventricles) and these chambers are connected to 4 blood vessels (aorta, vena cava, pulmonary artery, and pulmonary vein).

The valve between the left atrium and the left ventricle is called the mitral valve; the valve between the right atrium and the right ventricle is called the aortic valve; and the valve between the right atrium and the pulmonary artery is called the pulmonary valve.

The valves should open and close completely as the heart beats. Backflow of blood or flow disturbance occurs when the valve does not move smoothly, including incomplete closing or opening. Heart valve disease is classified as blood leakage because of the incomplete closure of the valve (regurgitation) or incomplete opening of the valve (stenosis).

Mitral regurgitation is a disease causing heart failure. The heart becomes strained from the backflow of blood caused by incomplete closure of the mitral valve between the left atrium and left ventricle.

The standard treatment for mitral stenosis is the repair of the mitral valve by incising the heart after opening the sternum, or replacing the valve with an artificial valve. This treatment is very effective, but it is very invasive with a mortality rate of up to 5%. Because of this mortality rate, treatment is usually confined to severe mitral stenosis. However, a newer treatment with percutaneous mitral valvuloplasty, in which the mitral valve is repaired through a simple procedure by means of a catheter, prevents the need for surgery that includes incising the heart after opening the chest.

In line with this newer treatment, the detailed description of mitral cerclage coronary sinus annuloplasty was published in an international journal (Kim et al., Mitral cerclage annuloplasty, a novel transcatheter treatment for secondary mitral valve regurgitation: initial results in swine. *Journal of American College Cardiology* 2009; 754(7):638-51) and described in an international patent application (WO2008/060553), which application is herein incorporated by reference in its entirety. The usefulness of this technique is attributed to the circular pressure that can be applied to the perimeter of the mitral annulus.

The technique for percutaneous mitral valvuloplasty is as follows. The right ventricle is accessed through the jugular vein, and the cerclage thread is passed though the proximal septal vein by positioning the catheter in the coronary sinus. The thread can then be fed through the right ventricular outflow tract (RVOT), into the right ventricle, and then into the tissue adjacent to the mitral annulus. The mitral annulus is constricted when tension is applied to the thread: incomplete closure is reduced by making the two valve leaflets come into closer contact. Constricting the mitral annulus reduces the backflow of blood through the mitral valve.

Routing of the thread is achieved with a guide wire to position the cerclage thread around the mitral annulus. After a sheath is passed along the guide wire, the cerclage thread is inserted into the sheath and the sheath is removed.

However, it is difficult to pass the cerclage thread through the curved sheath as the cerclage thread is not as rigid as the guide wire. This problem extends surgical time and can result in an unfavorable outcome for the patient.

In addition, the adjacent cardiac tissue is often damaged during constriction of the mitral annulus by the relatively rigid cerclage thread.

Patent literature 1) WO 2008/060553 (THE GOVERNMENT OF THE UNITED STATES OF AMERICA AS REPRESENTED BY THE SECRETARY OF THE DEPARTMENT OF HEALTH AND HUMAN SERVICES) May 22, 2008.

Patent literature 2) KR 1116867 (Joon Hong Kim) Feb. 8, 2012.

Non-Patent literature 1) Kim et al., Mitral cerclage annuloplasty, a novel transcatheter treatment for secondary mitral valve regurgitation: initial results in swine. *Journal of American College Cardiology* 2009; 54(7):638-51.

SUMMARY

The present invention is designed, in part, to solve the problem described earlier with the aim of providing a sheath for mitral valve cerclage annuloplasty, which comprises the cerclage thread in a lumen created independently from the lumen through which the guide wire is passed.

An additional purpose of the present invention is to provide a less rigid cerclage thread for use in mitral valve cerclage surgery.

The sheath of the present invention for mitral valve cerclage annuloplasty is designed, in part, to achieve the following purposes:

the sheath comprises a first lumen, in which a guide wire is passed, and a second lumen, through which a cerclage thread is passed.

This sheath carries the cerclage thread through the above second lumen.

In one embodiment, the second lumen passes through to the insertion end of the above sheath, such that the cerclage thread can pass through the insertion end of the sheath, as depicted in FIG. 3.

In another embodiment, the second lumen is closed at the insertion end of the above sheath, such that the cerclage thread can not pass through the insertion end of the sheath, as depicted in FIG. 4.

In one embodiment, the material of the cerclage thread is selected from: expanded polytetrafluoroethylene (ePTFE), polytetrafluoroethylene, poly(tetrafluoroethylene-co-hexafluoropropylene), perfluoroalkoxy, polyvinylidenefluoride, poly(ethylene-co-tetrafluoroethylene), polychlorotrifluoroethylene, polyethyleneterephthlate, polyetheretherketone, nylon, polyethylene, polyglecaprone, polyglactin, polybutylate, polyester, silk, polyamide, polypropylene, poly(hexafluoropropylene-vinylidenefluoride), silicone resin, poly(lactic acid) (PLA), poly(t-lactic acid) (PLLA), poly(D,L-lactic acid), polyglycol acid (PGA), poly(D-lactic acid-glycol acid copolymer), poly(L-lactic acid-glycol acid copolymer), poly(D,L-lactic acid-glycol acid copolymer), poly(caprolactone), poly(valerolactone), poly (hydroxybutylate), polydioxanone, poly(hydroxybutylate), poly(hydrovalerate), copolymer of trimethylene carbonate-glycolide, copolymer of polyglycolacid-caprolactone, copolymer of poly(lactic acid)-caprolactone, block copolymer of poly(lactic acid)-poly(ethylene glycol), poly(ethylene oxide)-poly(butylene terephthlate), poly(copolymer of lactic acid-trimethylene carbonate), poly(caprolactone copolymer), poly(L-lactic acid copolymer), polylactide, polyglycolide, poly(copolymer of lactic acid-glycolide), polyanhydride, polyorthoester, and groups made of a mixture of the above materials.

In one embodiment, the cerclage thread of the present invention is characterized by its location of insertion into the body above the mitral cerclage annuloplasty sheath in the second lumen.

In addition, in certain embodiments, the cerclage thread is made of a material selected from expanded polytetrafluoroethylene (ePTFE), polytetrafluoroethylene, poly(polytetrafluoroethylene-co-hexafluoropronylene), perfluoroalkoxy, polyvinylidenefluoride, poly(ethylene-co-tetrafluoroethylene), polychlorofluoroethylene, polyethyleneterephthlate, polyetheretherketone, nylon, polyethylene, polyglecaprone, polyglactin, polybutylate, polyester, silk, polyamide, polypropylene, poly(hexafluoroethylene-vinylidenefluoride), silicone resin, poly(lactic acid) (PLA), poly(t-lactic acid) (PLLA), poly(D,L-lactic acid), polyglycol acid (PGA), poly(D-lactic acid-glycolacid copolymer), poly(L-lactic acid-glycolacid copolymer), poly(D,L-lactic acid-glycolacid copolymer), poly(caprolactone), poly(valerolactone), poly (hydroxybutylate), polydioxanone, poly(hydroxybutylate), poly(hydrovalerate), copolymer of trimethylene carbonate and glycolide, copolymer of polyglycol acid and caprolactone, copolymer of poly(lactic acid) and caprolactone, block copolymer of poly(lactic acid)-poly(ethylene glycol), poly (ethylene oxide)-poly(butylene terephthlate), poly(copolymer of lactic acid-trimethylene carbonate), poly(caprolactone copolymer), poly(L-lactic acid copolymer), polylactide, polyglycolide, poly(copolymer of lactic acid-glycolide), polyanhydride, polyorthoester, or groups of a mixture of the above materials.

In one embodiment, the surface of the present invention cerclage thread is coated with medical substances, for example, antibiotics.

In another embodiment, the cerclage thread of the present invention includes multiple layers by using a first layer of a material with high tensile strength and by coating the first layer with a second layer of a material of high biocompatibility.

The inconvenience of putting the cerclage thread into a conventional sheath for mitral valve cerclage annuloplasty can be avoided in the present invention by having the cerclage thread inside the sheath before surgery. This has several advantages, such as, patient recovery is improved, the surgery is simpler, and the surgery time is reduced.

Moreover, the sheath for mitral valve cerclage annuloplasty in the present invention has the advantage that the cerclage thread can be made of a wide variety of materials, including materials that cannot be used for traditional cerclage annuloplasty due to their limited rigidity. In addition, the less rigid cerclage thread that can be used in the presently described sheath can reduce damage to the adjacent cardiac tissue in the course of constricting the perimeter of the mitral annulus. In addition, the wide variety of materials for the cerclage thread, include materials having excellent biocompatibility that can improve the success rate of the annuloplasty procedure.

DETAILED DESCRIPTION

Figure 1:
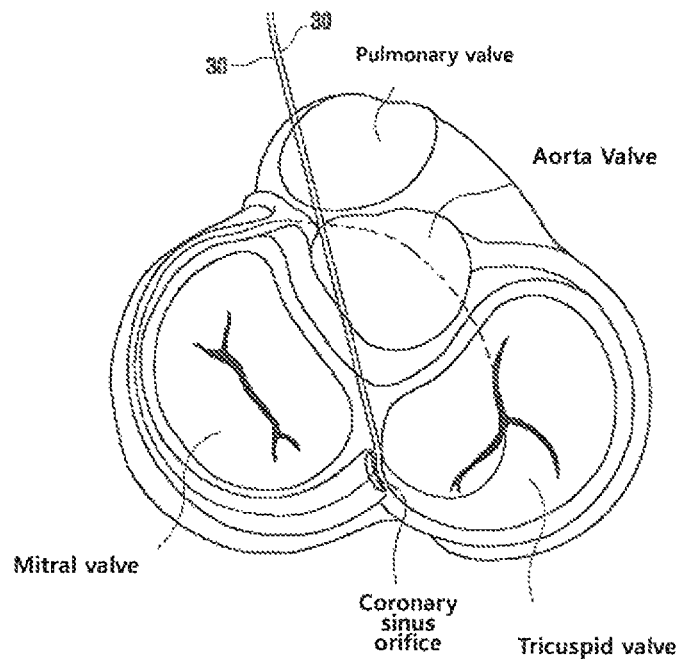
FIG. 1 is a cross-sectional diagram that depicts the constriction of the perimeter of the mitral annulus by the mitral valve cerclage annuloplasty.

Reference will now be made in detail to various exemplary embodiments, examples of which are illustrated in the accompanying drawings. It is to be understood that the following detailed description is provided to give the reader a fuller understanding of certain embodiments, features, and details of aspects of the invention, and should not be interpreted as a limitation of the scope of the invention.

The definitions of the terminology used in the detailed description are as follows: "mitral cerclage annuloplasty" refers to surgery needed to place the cerclage thread in the right ventricle through the jugular vein and then to a point on the RVOT, passing though the coronary sinus and proximal septal vein, and on to the right ventricle to be positioned near the mitral annulus, and to constrict the mitral annulus by increasing tension on the thread.

The term "cerclage thread" is the thread used to constrict the mitral annulus during mitral valve cerclage annuloplasty.

In addition, the end inserted into the body at the end of the sheath in the present invention is called the "insertion end" and the end located at the huh of the catheter at the opposite end is called the "proximal end."

The sheath for mitral valve cerclage annuloplasty in the present invention (10) is characterized by the creation of two lumens with the cerclage thread (30) placed inside one.

One of the above two lumens is the first lumen (12) through which the guide wire (20) is passed. When the guide wire (20) is positioned around the mitral annulus for mitral valve cerclage annuloplasty, the above sheath (10) is also positioned near the mitral annulus along the guide wire (20).

The insertion of the cerclage thread (30) into the sheath near the mitral annulus is performed in the usual way.

However, insertion of the cerclage thread (30) could be time consuming because it is less rigid than the guide wire (20). This could greatly inconvenience the surgeon and patient because it extends surgical time.

In one embodiment, the present invention is characterized by the insertion of the cerclage thread (30) into the lumen of the sheath (10) in advance of surgery.

Figure 2:
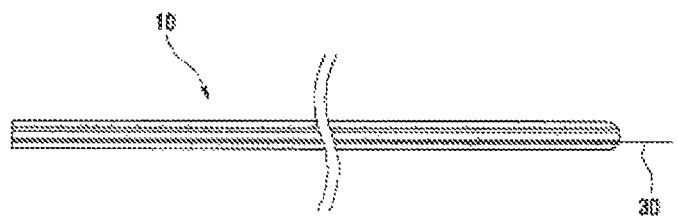
FIG. 2 shows the sheath for mitral valve cerclage annuloplasty.
Figure 3:
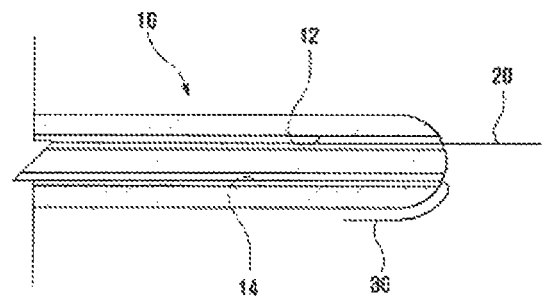
FIG. 3 shows the insertion end in FIG. 2.
Figure 4:
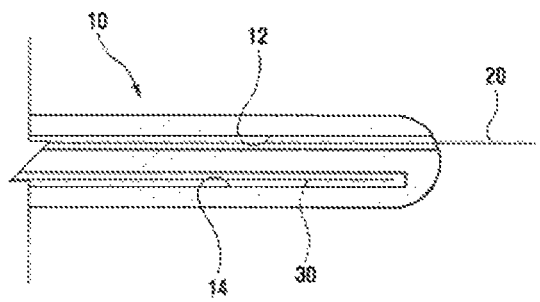
FIG. 4 presents another view of the insertion end in FIG. 2.
The references numbers used in the drawings are as follows:
10: Sheath for mitral valve cerclage annuloplasty in the present invention
14: The second lumen
20: Guide wire
30: Cerclage thread

FIG. 2 depicts one embodiment of the sheath for mitral valve cerclage annuloplasty in the present invention, and FIGS. 3 and 4 depict the sheath (10) insertion ends.

As depicted in the embodiments of FIGS. 2 and 4, insertion of the cerclage thread (30) during surgery is not necessary because the sheath for mitral valve cerclage annuloplasty in the present invention includes the cerclage thread (30) in the sheath (10).

Thus, this invention is advantageous, in part, because the cerclage thread (30) can be inserted into the sheath (10) before surgery, instead of inserting the cerclage thread (30) into the bent sheath during surgery, as performed in conventional mitral valve cerclage annuloplasty.

With regard to the insertion end of the sheath for mitral valve cerclage annuloplasty in the present invention (10), in certain embodiments, the cerclage thread (30) may pass through an open end of the second lumen as shown in FIG. 3, or the cerclage thread (30) may be contained within a closed end of the second lumen as shown in FIG. 4.

With regard to the cerclage thread (30) passing through the insertion end of the second lumen (14), it is desirable in certain embodiments to expose a part of the cerclage thread (30) as depicted in FIG. 3 to prevent the cerclage thread (30) from being pushed out when inserting the sheath (10) along the guide wire (20).

The sheath can be removed (10) by pulling the proximal end of the sheath (10) while holding the cerclage thread (30) at the insertion end of the sheath (10) in the jugular vein. In another way, it could be removed by pulling the insertion end of the sheath (10) while holding the cerclage thread (30) at the proximal end of the opposite side.

FIG. 4 shows the closed insertion end in the second lumen (14), with the advantage of the cerclage thread (30) not being pushed out during the insertion of the sheath (10). In this case, the sheath is removed (10) by pulling out the insertion end of the sheath (10) while holding the cerclage thread (30) at the proximal end side of the sheath (10).

The sheath for mitral valve cerclage annuloplasty in the present invention enables the use of cerclage thread made from various materials that cannot be used in the conventional method because the sheath is inserted into the body with the cerclage thread already present inside the second lumen.

According to the conventional method, the thread must be made of a rigid material, such as nylon, to allow the cerclage thread to be inserted into the sheath after implanting the sheath. The mitral valve cerclage annuloplasty constricts the tissue around the mitral annulus by passing the cerclage thread through the coronary sinus and proximal septal vein. Necrotic damage to the surrounding tissue is possible when applying tension over an extended period of time. This can be more severe when the cerclage thread is made of material having reduced biocompatibility.

However, the sheath for mitral valve cerclage annuloplasty in the present invention enables the use of a less rigid cerclage thread because pushing the cerclage thread into the sheath is avoided.

Thus, one advantage of the present invention is being able to use materials for the cerclage thread, such as expanded polytetrafluoroethylene (ePTFE), which have lower rigidity and/or higher biocompatibility, as compared to the cerclage threads used in conventional mitral valve cerclage annuloplasty.

Similarly, the sheath for mitral valve cerclage annuloplasty in the present invention may be made from a material selected from a fluoropolymer such as polytetrafluoroethylene, poly (tetrafluoroethylene-co-hexafluoropropylene), perfluoroalkoxy, polyvinylidenefluoride, poly(ethylene-co-tetrafluoroethylene), or polychlorotrifluoroethylene; a biocompatible polymer such as polyethyleneterephthlate, polyetheretherketone, nylon, polyethylene, polyglecaprone, polyglactin, polybutylate, polyester, silk, polyamide, polypropylene, poly (hexafluoropropylene-vinylidenefluoride), or silicone resin; a biodegradable copolymer such as poly(lactic acid) (PLA), poly(L-lactic acid) (PLLA), poly(D,L-lactic acid), polyglycol acid (PGA), poly(D-lactic acid-glycol acid copolymer), poly (L-lactic acid-glycol acid copolymer), poly(D,L-lactic acid-glycol acid copolymer), poly(caprolactone), poly(valerolactone), poly(hydroxybutylate), polydioxanone, poly (hydroxybutylate), poly(hydrovalerate), copolymer of trimethylente carbonate and glycolide, copolymer of polyglycolacid and caprolactone, copolymer of poly(lactic acid)-caprolactone, block copolymer of poly(lactic acid)-poly(ethylene glycol), poly(ethylene oxide)-poly(butylene terephthlate), poly(copolymer of lactic acid-trimethylene carbonate), poly(caprolactone copolymer), poly(L-lactic acid copolymer), polylactide, polyglycolide, poly(copolymer of lactic acid-glycolide), polyanhydride, or polyorthoester; or a mixture of the above-mentioned materials.

A cerclage thread made of these biocompatible polymers provides stable long-term tension with minimal damage to the adjacent biological tissues and improves the function of the mitral valve.

In certain embodiments, the present invention is characterized by a cerclage thread made of the above materials.

In other embodiments, the cerclage thread of present invention may prevent or reduce inflammatory reactions by coating the surface of the cerclage thread with a chemical substance, such as an antibiotic.

In one embodiment, the core layer of the cerclage thread comprises multiple layers. For example, the first layer may comprise a material with high tensile strength, which is coated with a second layer comprising a material with high biocompatibility. In this case, the coating of the second layer may be made by conventional methods, such as dip coating, ultrasonic spray, and electric spray.

ADDITIONAL EMBODIMENTS

Embodiment 1

A sheath for mitral valve cerclage annuloplasty, wherein the sheath forms a first lumen through which a guide wire passes, and a second lumen, wherein a cerclage thread is equipped within the above second lumen.

Embodiment 2

The sheath according to Embodiment 1, wherein the second lumen passes through to the insertion end of the above sheath.

Embodiment 3

The sheath according to Embodiment 1, wherein the second lumen is closed at the insertion end of the above sheath.

Embodiment 4

The sheath of Embodiments 1-3, wherein the materials of the above cerclage thread are expanded polytetrafluoroethylene (ePTFE), polytetrafluoroethylene, poly(tetrafluoroethylene-co-hexafluoropropylene), perfluoroalkoxy, polyvinylidenefluoride, poly(ethylene-co-tetrafluoroethylene), polychlorotrifluoroethylene, polyethyleneterephthlate, polyetheretherketone, nylon, polyethylene, polyglecaprone, polyglactin, polybutylate, polyester, silk, polyamide, polypropylene, poly(hexafluoropropylene-vinylidenefluoride), silicone resin, poly(lactic acid) (PLA), poly(L-lactic acid) (PLLA), poly(D,L-lactic acid), polyglycol acid (PGA), poly(D-lactic acid-glycol acid copolymer), poly(L-lactic acid-glycol acid copolymer), poly(D,L-lactic acid-glycol acid copolymer), poly(caprolactone), poly(valerolactone), poly(hydroxybutylate), polydioxanone, poly(hydroxybutylate), poly(hydrovalerate), copolymer of trimethylene carbonate-glycolide, copolymer of polyglycolacid-caprolactone, copolymer of poly(lactic acid)-caprolactone, block copolymer of poly(lactic acid)-poly(ethylene glycol), polyethylene oxide)-poly(butylene terephthlate), poly(copolymer of lactic acid-trimethylenecarbonate), poly(caprolactone copolymer), poly(L-lactic acid copolymer), polylactide, polyglycolide, poly(copolymer of lactic acid-glycolide), polyanhydride, or polyorthoester, and the sheath for mitral valve cerclage annuloplasty of the present invention is characterized by a selected mixture of these groups.

Embodiment 5

A cerclage thread for insertion into a body, wherein the cerclage thread is inserted into the body through the second lumen of the sheath for mitral valve cerclage annuloplasty of any one of Embodiments 1-3.

Embodiment 6

The cerclage thread of Embodiment 5, wherein the cerclage thread is made of a material selected form expanded polytetrafluoroethylene (ePTFE), polytetrafluorethylene, poly(tetrafluorethylene-co-hexafluorpropylene), perfluoroalkoxy, polyvinylidenfluoride, poly(ethylene-co-tetrafluorethylene), polychlorotrifluroethylene, polyethyleneterephthlate, polyetheretherketon, nylon, polyethylene, poliglecaprone, polyglactin, polybutylate, polyesther, silk, polyamide, polypropylene, poly(hexafluorpropylene-vinyllidenfluoride) (Poly(hexafluoropropylene-VDF)), silicone resin, poly(lactic acid) (PLA), poly(L-lactic acid) (PLLA), poly(D,L-lactic acid), polyglycol acid (PGA), poly(D-lactic acid-glycol acid copolymer), poly(L-lactic acid-glycol acid copolymer), poly(D,L-lactic acid-glycol acid copolymer), poly(caprolacton), poly(valerolactone), poly(hydroxybutylate), poly dioxanone, poly(hydroxybutylate), poly(hydrovalerate), copolymer of trimethylentcargonate and glycolide, copolymer of polyglycolacid and caprolacton, copolymer of poly(lactic acid) and caprolacton, block copolymer of poly(lactic acid)-poly(ehtyleneglyco), poly(ethyleneoxide)-poly(butyleneterephthlate), poly(copolymer of lactic acid-trimethylenecarbonate), poly(caprolacton copolymer), poly(L-lactic acid copolymer), poly lactide, poly glycolide, poly(copolymer of lactic acid-glycolide), poly anhydride, poly orthoesther or the sheath for mitral valve cerclage annuloplasty of present invention characterized with the selection from the mixture of these groups.

Embodiment 7

A cerclage thread for mitral valve cerclage annuloplasty, wherein the cerclage thread is made of a material selected from expanded polytetrafluoroethylene (ePTFE), polytetrafluorethylene, poly(tetrafluorethylene-co-hexafluorpropylene), perfluoroalkoxy, polyvinylidenfluoride, poly(ethylene-co-tetrafluorethylene), polychlorotrifluroethylene, polyethyleneterephthlate, polyetheretherketon, nylon, polyethylene, poliglecaprone, polyglactin, polybutylate, polyesther, silk, polyamide, polypropylene, poly(hexafluorpropylene-vinyllidenfluoride) (Poly(hexafluoropropylene-VDF)), silicone resin, poly (lactic acid)(PLA), poly(L-lactic acid) (PLLA), poly(D,L-lactic acid), polyglycol acid (PGA), poly (D-lactic acid-glycol acid copolymer), poly(L-lactic acid-glycol acid copolymer), poly(D,L-lactic acid-glycol acid copolymer), poly(caprolacton), poly(valerolactone), poly(hydroxybutylate), poly dioxanone, poly(hydroxybutylate), poly(hydrovalerate), copolymer of trimethylentcargonate and glycolide, copolymer of polyglycolacid and caprolacton, copolymer of poly(lactic acid) and caprolacton, block copolymer of poly(lactic acid)-poly(ehtyleneglyco), poly(ethyleneoxide)-poly(butyleneterephthlate), poly(copolymer of lactic acid-trimethylenecarbonate), poly(caprolacton copolymer), poly(L-lactic acid copolymer), poly lactide, poly glycolide, poly(copolymer of lactic acid-glycolide), poly anhydride, poly orthoesther and the cerclage thread for sheath for mitral valve cerclage annuloplasty of present invention characterized with the selection from the mixture of these groups.

While this invention has been particularly shown and described with references to preferred embodiments thereof, it will be understood by those skilled in the art that various changes in form and details may be made therein without departing from the scope of the invention encompassed by the appended claims.

What is claimed is:
1. A device for mitral valve cerclage annuloplasty, comprising:
    a guide wire;
    a cerclage thread; and
    a sheath comprising a proximal end and an insertion end;
    wherein the sheath consists of a first lumen through which the guide wire passes, and a second lumen, wherein the cerclage thread is inserted within the second lumen;
    wherein the cerclage thread is contained within a closed end of the second lumen at the insertion end of the sheath; and
    wherein the first and second lumens run parallel to a central axis of the sheath and extend substantially the length of the sheath.
2. The device of claim 1, wherein the cerclage thread is made of a material selected from:
    expanded polytetrafluoroethylene (ePTFE), polytetrafluoroethylene, poly(tetrafluoroethylene-co-hexafluoropropylene), perfluoroalkoxy, polyvinylidenefluoride, poly(ethylene-co-tetrafluoroethylene), polychlorotrifluoroethylene, polyethyleneterephthlate, polyetheretherketone, nylon, polyethylene, polyglecaprone, polyglactin, polybutylate, polyester, silk, polyamide, polypropylene, poly(hexafluoropropylene-vinylidenefluoride), silicone resin, poly(lactic acid) (PLA), poly(L-lactic acid) (PLLA), poly(D,L-lactic acid), polyglycol acid (PGA), poly(D-lactic acid-glycol acid copolymer), poly(L-lactic acid-glycol acid copolymer), poly(D,L-lactic acid-glycol acid copolymer), poly(caprolactone), poly(valerolactone), poly(hydroxybutylate), polydioxanone, poly(hydroxybutylate), poly(hydrovalerate), copolymer of trimethylene carbonate-glycolide, copolymer of polyglycolacid-caprolactone, copolymer of poly(lactic acid)-caprolactone, block copolymer of poly(lactic acid)-poly(ethylene glycol), polyethylene oxide)-poly(butylene terephthlate), poly(copolymer of lactic acid-trimethylenecarbonate), poly(caprolactone copolymer), poly(L-lactic acid copolymer), polylactide, polyglycolide, poly(copolymer of lactic acid-glycolide), polyanhydride, or polyorthoester.

3. The device of claim 1, wherein the cerclage thread is inserted into the second lumen before the sheath is inserted into a patient undergoing mitral valve cerclage annuloplasty.

4. The device of claim 3, wherein the cerclage thread is made of a material selected from:

expanded polytetrafluoroethylene (ePTFE), polytetrafluoroethylene, poly(tetrafluoroethylene-co-hexafluoropropylene), perfluoroalkoxy, polyvinylidenefluoride, poly(ethylene-co-tetrafluoroethylene), polychlorotrifluoroethylene, polyethyleneterephthlate, polyetheretherketone, nylon, polyethylene, polyglecaprone, polyglactin, polybutylate, polyester, silk, polyamide, polypropylene, poly(hexafluoropropylene-vinylidenefluoride), silicone resin, poly(lactic acid) (PLA), poly(L-lactic acid) (PLLA), poly(D,L-lactic acid), polyglycol acid (PGA), poly(D-lactic acid-glycol acid copolymer), poly(L-lactic acid-glycol acid copolymer), poly(D,L-lactic acid-glycol acid copolymer), poly(caprolactone), poly(valerolactone), poly(hydroxybutylate), polydioxanone, poly(hydroxybutylate), poly(hydrovalerate), copolymer of trimethylene carbonate-glycolide, copolymer of polyglycolacid-caprolactone, copolymer of poly(lactic acid)-caprolactone, block copolymer of poly(lactic acid)-poly(ethylene glycol), polyethylene oxide)-poly(butylene terephthlate), poly(copolymer of lactic acid-trimethylenecarbonate), poly(caprolactone copolymer), poly(L-lactic acid copolymer), polylactide, polyglycolide, poly(copolymer of lactic acid-glycolide), polyanhydride, or polyorthoester.

5. The device of claim 1, wherein the sheath is configured to position the cerclage thread such that the cerclage thread provides circumferential support to a mitral valve annulus when the sheath is removed from a puncture site following the annuloplasty.

6. The device of claim 5, wherein the cerclage thread is made of a material selected from:

expanded polytetrafluoroethylene (ePTFE), polytetrafluoroethylene, poly(tetrafluoroethylene-co-hexafluoropropylene), perfluoroalkoxy, polyvinylidenefluoride, poly(ethylene-co-tetrafluoroethylene), polychlorotrifluoroethylene, polyethyleneterephthlate, polyetheretherketone, nylon, polyethylene, polyglecaprone, polyglactin, polybutylate, polyester, silk, polyamide, polypropylene, poly(hexafluoropropylene-vinylidenefluoride), silicone resin, poly(lactic acid) (PLA), poly(L-lactic acid) (PLLA), poly(D,L-lactic acid), polyglycol acid (PGA), poly(D-lactic acid-glycol acid copolymer), poly(L-lactic acid-glycol acid copolymer), poly(D,L-lactic acid-glycol acid copolymer), poly(caprolactone), poly(valerolactone), poly(hydroxybutylate), polydioxanone, poly(hydroxybutylate), poly(hydrovalerate), copolymer of trimethylene carbonate-glycolide, copolymer of polyglycolacid-caprolactone, copolymer of poly(lactic acid)-caprolactone, block copolymer of poly(lactic acid)-poly(ethylene glycol), polyethylene oxide)-poly(butylene terephthlate), poly(copolymer of lactic acid-trimethylenecarbonate), poly(caprolactone copolymer), poly(L-lactic acid copolymer), polylactide, polyglycolide, poly(copolymer of lactic acid-glycolide), polyanhydride, or polyorthoester.

* * * * *